(12) United States Patent
Kell et al.

(10) Patent No.: US 9,322,332 B2
(45) Date of Patent: Apr. 26, 2016

(54) INSPECTION DEVICE FOR AN INTERNAL COMBUSTION ENGINE

(71) Applicant: ROLLS-ROYCE PLC, London (GB)

(72) Inventors: James Kell, Nottingham (GB); Adriano Pulisciano, Birmingham (GB); Thomas Frederick Danvers, Derbyshire (GB); Graeme Eric Rigg, Derby (GB)

(73) Assignee: ROLLS-ROYCE plc, London (GB)

( * ) Notice: Subject to any disclaimer, the term of this patent is extended or adjusted under 35 U.S.C. 154(b) by 581 days.

(21) Appl. No.: 13/788,906

(22) Filed: Mar. 7, 2013

(65) Prior Publication Data
US 2013/0247540 A1 Sep. 26, 2013

(30) Foreign Application Priority Data

Mar. 21, 2012 (GB) .................................. 1204913.6

(51) Int. Cl.
*F02C 7/00* (2006.01)
*F01D 21/00* (2006.01)

(52) U.S. Cl.
CPC ................ *F02C 7/00* (2013.01); *F01D 21/003* (2013.01); *F05D 2260/80* (2013.01)

(58) Field of Classification Search
CPC ..... F02C 7/00; F01D 21/003; F05D 2260/80; G01M 15/108; G01M 15/14; G01L 23/16
USPC .......... 73/114.09; 415/118; 356/241.1–241.5; 123/143 B
See application file for complete search history.

(56) References Cited

U.S. PATENT DOCUMENTS

| | | | | |
|---|---|---|---|---|
| 4,666,297 A | * | 5/1987 | Suarez-Gonzalez .. | F01D 17/085 356/43 |
| 4,787,053 A | * | 11/1988 | Moore ..................... | F01D 21/00 340/945 |
| 6,091,489 A | * | 7/2000 | Welker ............... | G02B 23/2407 356/241.1 |

FOREIGN PATENT DOCUMENTS

| | | |
|---|---|---|
| GB | 2 244 047 A | 11/1991 |
| JP | A-2001-349535 | 12/2001 |
| SU | 1321844 A1 | 7/1987 |

OTHER PUBLICATIONS

Jul. 17, 2012 British Search Report issued in British Patent Application No. GB1204913.6.

* cited by examiner

*Primary Examiner* — Alexander Comley
*Assistant Examiner* — Kenneth J Hansen
(74) *Attorney, Agent, or Firm* — Oliff PLC

(57) ABSTRACT

This invention relates to an internal combustion engine having a cavity for inspection, comprising: an inspection device mounted within a housing, the housing at least partially located within the cavity to be inspected and having a shutter which is actuable between a closed configuration and an open configuration; and an actuation mechanism for moving the shutter between the closed configuration and the open configuration.

15 Claims, 2 Drawing Sheets

INSPECTION DEVICE FOR AN INTERNAL COMBUSTION ENGINE

TECHNICAL FIELD OF INVENTION

This invention relates to an inspection device for an internal combustion engine.

BACKGROUND OF INVENTION

FIG. 1 shows a ducted fan gas turbine engine 10 comprising, in axial flow series: an air intake 12, a propulsive fan 14 having a plurality of fan blades 16, an intermediate pressure compressor 18, a high-pressure compressor 20, a combustor 22, a high-pressure turbine 24, an intermediate pressure turbine 26, a low-pressure turbine 28 and a core exhaust nozzle 30. A nacelle 32 generally surrounds the engine 10 and defines the intake 12, a bypass duct 34 and a bypass exhaust nozzle 36.

Air entering the intake 12 is accelerated by the fan 14 to produce a bypass flow and a core flow. The bypass flow travels down the bypass duct 34 and exits the bypass exhaust nozzle 36 to provide the majority of the propulsive thrust produced by the engine 10. The core flow enters in axial flow series the intermediate pressure compressor 18, high pressure compressor 20 and the combustor 22, where fuel is added to the compressed air and the mixture burnt. The hot combustion products expand through and drive the high, intermediate and low-pressure turbines 24, 26, 28 before being exhausted through the nozzle 30 to provide additional propulsive thrust. The high, intermediate and low-pressure turbines 24, 26, 28 respectively drive the high and intermediate pressure compressors 20, 18 and the fan 14 by interconnecting shafts 38, 40, 42.

It is known in modern gas turbine engines 10 to use a boroscope to inspect the interior of the engine 10 both after assembly and during servicing to detect the fitness of the engine 10. Thus, engines 10 are known to have inspection ports in various locations to allow boroscopes to be inserted. FIG. 2 shows such a port 210 for a compressor 18 which includes an outer casing wall 212 and an inner casing wall 214 which house annular arrays of compressor rotor blades 216 and stator vanes 218. The port 210 includes flanged apertures 220, 222 through the inner 214 and outer 212 walls and is shown in a closed configuration in which the apertures 220, 222 are sealed with a plug 224. In this known example, the plug 224 constitutes sealing members 226, 228 for the inner and outer wall apertures 220, 222 which are linked by a link rod 230. The plug 224 can be realisably secured within the port 210 in any suitable manner and configured to be removed from the exterior of the compressor 18 when boroscope access is required. As will be appreciated, once removed, a boroscope can be inserted as required.

Typically, the inspection ports 210 are located around the engine core so that, for example, each stage of the compressor 18 may have a circumferential distribution of inspection ports, as might the combustor or various turbine stages.

The present invention seeks to provide an improved way of inspecting the interior of an internal combustion engine.

STATEMENTS OF INVENTION

In a first aspect, the present invention provide an internal combustion engine having a cavity for inspection, comprising: an inspection device mounted within a housing, the housing at least partially located within the cavity to be inspected and having a shutter which is actuable between a closed configuration and an open configuration; and an actuation mechanism for moving the shutter between the closed configuration and the open configuration.

Providing an inspection device behind a shutter allows the inspection device to be left in situ and used whenever the engine conditions allow. For example, in the case of a gas turbine engine, the inspection device may be placed within a section of compressor and exposed to view the operation of the compressor during start up or close down periods when the temperature is not excessive. Having an inspection device can provide important information about the operation of the engine and can aid engine health monitoring schemes.

The inspection device may be configured to allow visual inspection of the cavity. The inspection device may be an optical device. The optical device may comprise a camera. The optical device may be configured to receive infrared spectrum. In an alternative embodiment, the optical device may be a fibre optic cable or other light channeling medium or conduit. The optical device may be coupled to a light sensor which is remote to the inspection device.

The inspection device may be retractable between a stowed position and an inspection position.

The shutter may be retractably stowed within the housing when in the closed configuration and actuated into the cavity so as to expose the inspection device when in the open configuration.

The shutter may be configured to be actuated by the inspection device when the inspection device is moved between the stowed and inspection positions. The shutter may be acutable so as to move laterally across a field of view of the inspection device when moving between the open and closed configurations. The shutter may include a cleaning device for cleaning the inspection device.

The shutter and inspection device may be simultaneously actuable. The inspection device, actuation mechanism and shutter may comprise a single module which includes one part of a two part mounting system for mounting the device to the engine. The mounting system may be a threaded bore and corresponding boss or flange.

The actuation mechanism may be one taken from the group including pneumatic, hydraulic or electrical. The actuation mechanism may be linear or rotary.

The housing may be at least partially formed by a wall of the cavity. The cavity may include moving parts of the internal combustion engine.

The shutter may include first and second shutter plates. The first and second shutter plates may be symmetrically arranged. The shutter may be cup shaped. The shutter plates may be pivotably mounted. The shutter plates may be biased against a restraining element which retains the shutter plates in place when in the closed position. Upon actuating the shutter from the closed configuration to the open configuration may include moving the shutter plates relative to the restraining element such that the bias results in the inspection device being exposed to the cavity.

The internal combustion engine may be a gas turbine engine.

In a second aspect, the present invention provides an aircraft having the internal combustion engine according to the first aspect.

The actuation mechanism may be operable from the cockpit of an aircraft or as part of an engine health monitoring system.

DESCRIPTION OF DRAWINGS

Embodiments of the invention will now be described with the aid of the following drawings of which.

DETAILED DESCRIPTION OF INVENTION

Figure 1:
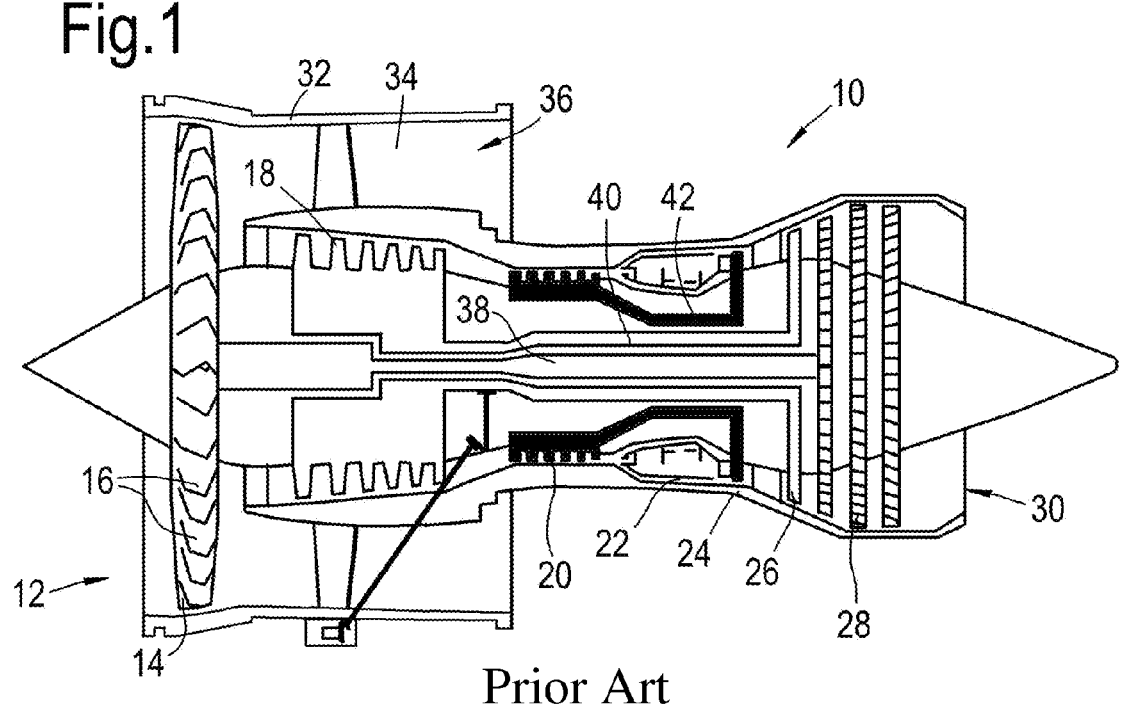
FIG. 1 shows a typical gas turbine engine.
Figure 2:
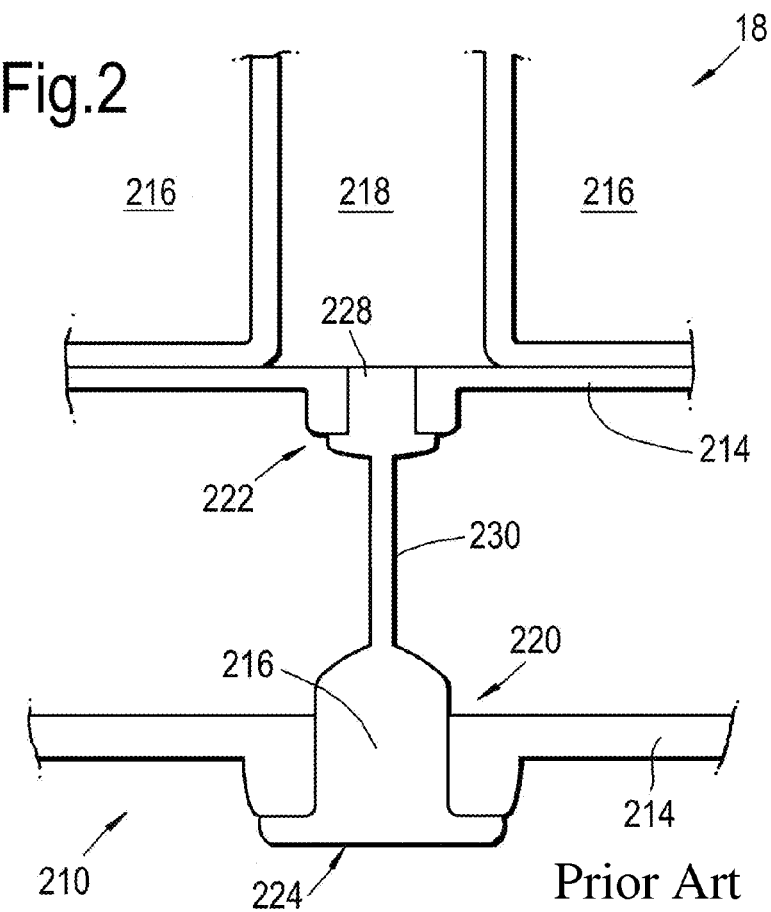
FIG. 2 shows a known arrangement for a boroscope inspection port.

FIG. 3 shows a portion of an internal combustion engine 310 in the form of a compressor wall 312 of a gas turbine engine, similar to the one shown in FIG. 2. The wall 312 is adjacent to the gas flow path 314 of the compressor which represents a cavity 316. As noted above, inspecting such a cavity can be beneficial for determining the condition of the engine, both prior to use and during a service interval.

Figure 3A:
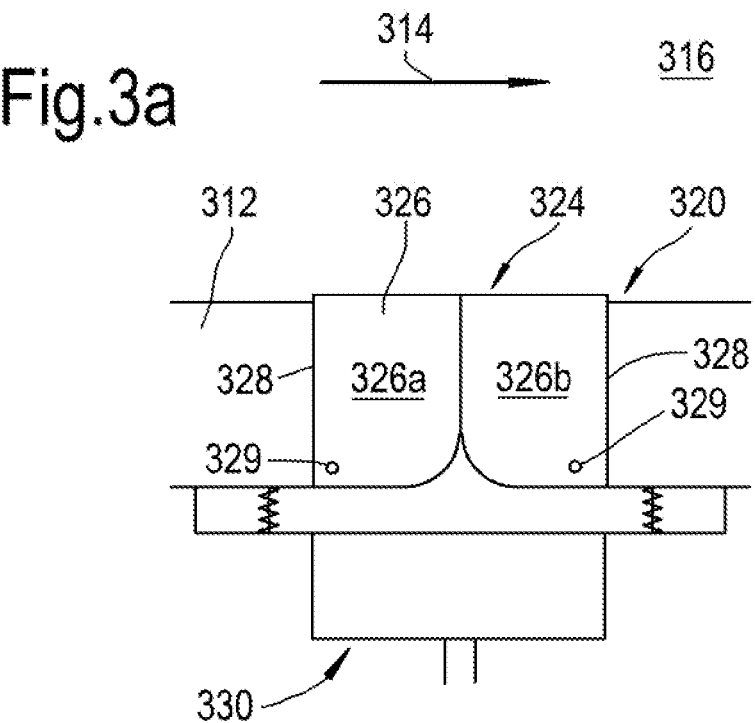
FIGS. 3a and 3b show a retractable inspection device in a stowed and inspection position accordingly.
Figure 3B:
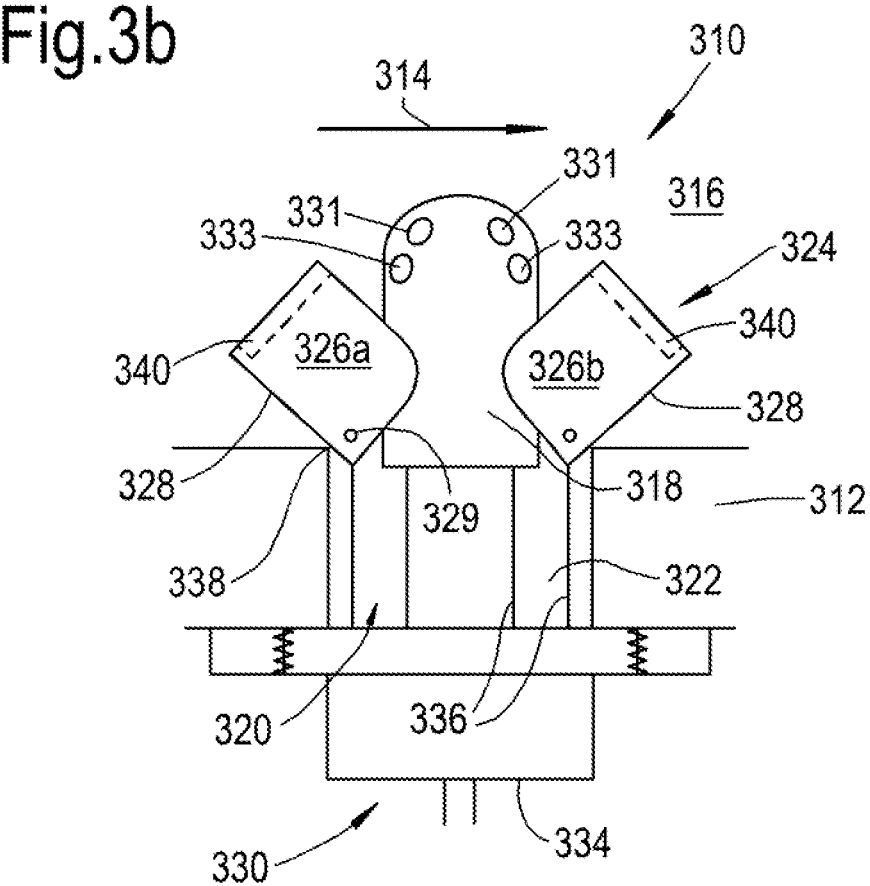

The engine 310 includes an inspection device 318 in the form of a camera which is mounted within a housing 320. In the described embodiment, the housing is in the form of an aperture 322 in the compressor wall 312. The inspection device 318 is retractably mounted in the housing 320 so as to be movable between a stowed position (as shown in FIG. 3a) where the inspection device 312 is shielded from the environment of the cavity, and an inspection position (as shown in FIG. 3b) in which the inspection device 318 is exposed to the cavity so as to allow inspection.

The engine 310 also includes a shutter 324 which provides an environmental shield for the inspection device 318 in the stowed position. The shutter 324 is arranged to be actuable between a closed configuration (FIG. 3a) and an open configuration (FIG. 3b). In the described embodiment, the shutter 324 is also retractably mounted within the housing 320 so as to have a stowed position which corresponds to the closed configuration, and an inspection position which corresponds to the open configuration.

The shutter 324 includes a cup shaped shield 326 having an internal chamber which fits over and receives the inspection device 318 when in the stowed position. The cup shaped shield 326 is inverted within the housing aperture 322 such that a base 326 of the cup faces the gas flow path 314 with the side walls 328 being snugly received within the aperture 322 of the compressor wall 312, with the inspection device 318 located within the internal chamber of the shutter 324. In this way, the shutter 324 and housing 320 combine to provide an enclosed protective space for the inspection device 318, with the base of the shutter 324 shielding the inspection device 318 from the cavity 316.

The shutter 324 is made from two shutter plates 326a, 326b which are similar to each other in construction and arranged in a symmetrically opposing manner so as to each provide half of the cup shaped shield 326 when in a closed configuration. Each shutter plate 326a, 326b is pivotably mounted 329 to an actuation mechanism 330 towards a distal end of the shutter 324 relative to the cavity such that, when they are not constrained by the housing 320, rotating the shutter plates 326a, 326b, about the pivot 329 results in each shutter plate 326a, 326b being moved away from the inspection device 318 to expose it to the cavity 316.

As the shutter plates 326a, 326b are symmetrically arranged, they form a pincer or scissor-like arrangement such that the cup-like structure of the shutter 324 pivotably parts along a midline so as to reveal the inspection device 318.

As described above, the shutter 324 can be thought of a shield to protect the inspection device 318 from the ambient operating environment which may be beyond the safe operating environment for the inspection device 318. For example, in the case of a compressor, the in use operating temperature may be several hundred degrees which would damage the inspection device 318. Thus, in this case, the shutter acts as a thermal shield and may be made from any suitable temperature resistant metal alloy or ceramic as known in the art.

The inspection device 318 of the embodiment is a camera. The camera may be configured to detect infrared emitted within the compressor but it will be appreciated that other visual and non-visual inspection devices may be advantageously used depending on the application. Having an infrared camera is particularly advantageous as it allows the thermal condition of the engine to be analysed during, for example, a wind down period. This can provide an invaluable insight into the condition of the engine and allow detection of flaws in components.

In the described embodiment, the camera is arranged to sense visible light and includes a wide angle lens 331 in the form of a 150 degree lens and a plurality of LEDs 333 to illuminate the interior of the cavity to be inspected.

In another embodiment, the inspection device is in the form of a light channeling medium or conduit such as fibre optic cable or light pipe which terminates at 331 as shown in FIG. 3b, in view of the cavity. Such a fibre optic may include the aforementioned wide angle lens. The camera, or sensor which detects the light, is located remote to the cavity. Thus, once exposed to the cavity, the end of the fibre optic 331 collects light from the cavity and channels them to the sensor which detects them. It will be appreciated that the sensor will have some associated electronics to process the signal of the sensed image which may or may not be local to the sensor. In this way, the shielding requirements may be much reduced as sensitive electronic components associated with the sensor and signal processing equipment need not be protected from the environment of the cavity to the same degree.

As described above, the inspection device 318 is retractable between a stowed position and an inspection position in conjunction with the shutter plates 326a, 326b, (FIGS. 3a and 3b respectively). An actuation mechanism 330 is included in the arrangement and is operable to move the inspection device 318 and shutter 324 between the stowed position and the inspection position.

The actuation mechanism 330 of the described embodiment is a linear actuator 332 which is operable to retract and deploy the inspection device 318 and shutter 324 simultaneously. Thus, the actuation mechanism 330 includes driving mechanism 332 located within a actuation housing 334. The driving mechanism 332 is linked to the shutter 324 and inspection device 318 via push rods 326 which are operably extended in use after an appropriate driving signal is provided. The type of linear actuator and driving mechanism 332 may be hydraulic, pneumatic or electrical and it will be appreciated that non-linear, e.g. rotary, actuators may also be suitably applied.

As will be appreciated, the actuation of the shutters 324 can be achieved in multiple ways. In one advantageous embodiment, the shutter plates 326a, 326b, are resiliently biased against a restraining element in the form of the walls of the housing aperture 322 such that pushing the shutter 324 into the cavity 316 results in the lateral movement and associated opening of the shutter plates 326a, 326b. Withdrawing the shutter 324 back into the recess causes the shutter plates 326a, 326b to contact the shoulder 338 of the housing aperture 322 which rotates the plates 326a, 326b about the pivot, thereby closing them.

The inside surface of the shutter 324 which faces the inspection device 318 lens (or sensor as the case may be) may include a cleaning device 340 which acts to clean the inspection device 318 upon opening of the shutter plates 326a, 326b and the associated lateral movement. In one advantageous embodiment, the cleaning device 340 may be a cloth or bristled structure.

The inspection device 318 arrangement may be inserted into the housing aperture 322 and secured by any known means. In one embodiment, the inspection device 318 and shutter 324 are threadingly engaged within the compressor wall 320 such that they can be removed for maintenance purposes. In this case, the shutter 324, inspection device 318 and actuation mechanism 330 are constructed and presented to the engine 310 as a single module.

Providing an inspection device 318 behind a shutter 324 allows the inspection device 318 to be left in situ and used whenever the engine conditions allow. For example, in the case of a gas turbine engine 10, the inspection device 318 may be placed within a section of compressor and exposed to view the operation of the compressor during start up or close down periods when the temperature is not excessive, but while it is still hot enough to give off a useful thermal signature. Having an inspection device can provide important information about the operation of the engine and can aid engine health monitoring schemes. Arranging the device to be retractable is particularly advantageous as it allows a broader field of view to be accommodated.

Thus, in use, upon engine shut down, the actuator mechanism 330 is energised so as to push the device into the gas stream flow path 314 to allow the wide angle lens 331 to view the rotating components as they windmill down to stop. Once the rotation speed is low enough to enable a sufficient video capture rate, the rotations are recorded and logged directly to the EMU (Engine Monitoring Unit). Once the required capture is complete, the actuation mechanism 330 pulls the device back into the aperture 322 and the shutter is closed so as to seal off the gas path.

Although not shown, the inspection device 318 arrangement also includes a means of removing the data captured by the camera. Hence, the inspection device 318 may be hard wired to the EMU or could be wirelessly connected.

It will be appreciated that the trigger for energising the actuation mechanism 330 may be automatic or may be provided by an operator. The operator may be local to the engine, for example, a pilot or maintenance staff, or may be a remote monitor such as an engine health monitoring system.

As will be appreciated, the above described embodiments are illustrative of the broader inventive concept which is defined by the appended claims. As such other variations on the above described embodiments will be possible.

For example, although the invention is described primarily from a view point of being used on a compressor of a gas turbine engine 10, it will be appreciated that the invention is applicable to various types of internal combustion engine and may be implemented at various locations around such an engine. For example, in the case of a gas turbine engine, the invention may be utilised in the compressor, combustor, or any other area in which active inspection may be beneficial. Further, there may be annular arrays of the inspection devices 318 around a given compressor stage so as to give a fuller, if not complete, view.

In other embodiments of the invention, the shutter 324 may include a single plate or an iris like structure. Further, the shutter may not be retractable with the inspection device but may be configured to move laterally with respect to the inspection device and housing aperture. Further still, the inspection device may be suitable type which may provide valuable data, such as a thermocouple, visible light spectrum, or pressure to name a few.

The invention claimed is:

1. An internal combustion engine having a cavity for inspection, comprising:
    an inspection device mounted within a housing, the housing at least partially located adjacent the cavity to be inspected and having a shutter which is actuable between a closed configuration and an open configuration, wherein the inspection device is retractable between a stowed position and an inspection position; and
    an actuation mechanism for moving the shutter between the closed configuration and the open configuration, wherein the shutter is configured to be actuated by the inspection device when the inspection device is moved between the stowed and inspection positions.

2. An internal combustion engine as claimed in claim 1, wherein the inspection device is configured to allow visual inspection of the cavity.

3. An internal combustion engine as claimed in claim 1, wherein the shutter is retractably stowed within the housing when in the closed configuration and actuated into the cavity so as to expose the inspection device when in the open configuration.

4. An internal combustion engine as claimed in claim 1, wherein the shutter includes a cleaning device for cleaning the inspection device.

5. An internal combustion engine as claimed in claim 1, wherein the shutter and inspection device are simultaneously actuable.

6. An internal combustion engine as claimed in claim 1, wherein the actuation mechanism is one taken from the group including pneumatic, hydraulic or electrical.

7. An internal combustion engine as claimed in claim 1, wherein the housing is at least partially formed within a wall of the cavity.

8. An internal combustion engine as claimed in claim 1, wherein the cavity includes moving parts of the internal combustion engine.

9. An internal combustion engine as claimed in claim 1, wherein the shutter includes a cup shaped shield, the cup shaped shield having an internal chamber which fits over and receives the inspection device when in the stowed position.

10. An internal combustion engine as claimed in claim 1, wherein the shutter includes at least one shutter plate which is biased against a restraining element so as to retain the shutter plate in place when in a closed configuration, and where actuating the shutter from the closed configuration to the open configuration includes moving the shutter plate relative to the restraining element such that the bias results in the inspection device being exposed to the cavity.

11. An internal combustion engine as claimed in claim 1, wherein the shutter includes first and second shutter plates.

12. An internal combustion engine as claimed in claim 1, wherein the internal combustion engine is a gas turbine engine.

13. An aircraft having the internal combustion engine as claimed in claim 1.

14. An aircraft as claimed in claim 13, wherein the actuation mechanism is operable from the cockpit of an aircraft or as part of an engine health monitoring system.

15. An internal combustion engine having a cavity for inspection, comprising:
    an inspection device mounted within a housing, the housing at least partially located adjacent the cavity to be inspected and having a shutter which is actuable between a closed configuration and an open configuration, wherein the inspection device is retractable between a stowed position and an inspection position; and an actuation mechanism for moving the shutter between the closed configuration and the open configuration, wherein the shutter includes a cup shaped shield, the cup shaped shield having an internal chamber which fits over and receives the inspection device when in the stowed position.

\* \* \* \* \*